US011186813B2

(12) United States Patent
Curel et al.

(10) Patent No.: US 11,186,813 B2
(45) Date of Patent: Nov. 30, 2021

(54) METHOD AND DEVICE FOR PLACING DISKS, SUCH AS ANTIBIOTIC DISKS

(71) Applicant: INTELLIGENCE ARTIFICIELLE APPLICATIONS, Montpellier (FR)

(72) Inventors: Christian Curel, Laverune (FR); Michel Roch, Saint Bres (FR); Jean-Louis Cariou, Aubais (FR)

(73) Assignee: INTELLIGENCE ARTIFIICIELLE APPLICATIONS, Montpellier (FR)

( * ) Notice: Subject to any disclaimer, the term of this patent is extended or adjusted under 35 U.S.C. 154(b) by 311 days.

(21) Appl. No.: 16/347,276

(22) PCT Filed: Oct. 30, 2017

(86) PCT No.: PCT/FR2017/052987
§ 371 (c)(1),
(2) Date: May 3, 2019

(87) PCT Pub. No.: WO2018/087451
PCT Pub. Date: May 17, 2018

(65) Prior Publication Data
US 2019/0276792 A1    Sep. 12, 2019

(30) Foreign Application Priority Data

Nov. 8, 2016 (FR) ..................... 16 60775

(51) Int. Cl.
*C12M 1/00* (2006.01)
*C12Q 1/18* (2006.01)
(Continued)

(52) U.S. Cl.
CPC .............. *C12M 99/02* (2013.01); *C12Q 1/18* (2013.01); *G01N 35/0099* (2013.01); *G01N 35/1002* (2013.01)

(58) Field of Classification Search
CPC ..... C12M 99/02; C12Q 1/18; G01N 35/0099; G01N 35/1002; B01L 2300/0609; B01L 2400/0478
See application file for complete search history.

(56) References Cited

U.S. PATENT DOCUMENTS 3,300,087 A     1/1967 Kuypers
5,377,865 A *  1/1995 Thomson ............... C12M 99/00
                                                        221/93

(Continued)

FOREIGN PATENT DOCUMENTS

FR         2933079 A1 *   1/2010  ......... G01N 35/1002
GB         1496015         12/1977
WO    WO-2010026506 A2 *  3/2010  ............ C12M 99/00

OTHER PUBLICATIONS

International Search Report dated Jan. 12, 2018.

*Primary Examiner* — Jill A Warden
*Assistant Examiner* — John McGuirk
(74) *Attorney, Agent, or Firm* — IPSILON USA, LLP

(57) ABSTRACT

A device for placing disks contained in a cartridge comprises a disk cartridge receiving area, a piston, means for moving the piston between a high position and a low position to enable, in the state in which a disk is positioned in the path followed by the piston during the transition from the high position to the low position of the piston, the disk to be placed on a surface vertically in line with the disk, a transfer system capable of transferring a disk from the cartridge in the cartridge receiving area to a location, arranged in the path to be followed by said piston, the said transit area. The device comprises a disk motion assist guide positionable in the transit area and moveable in a direction parallel to the up and down direction of movement of the piston.

10 Claims, 11 Drawing Sheets

(51) Int. Cl.
*G01N 35/00* (2006.01)
*G01N 35/10* (2006.01)

(56) References Cited

U.S. PATENT DOCUMENTS

2012/0277905 A1\* 11/2012 Botma ............... G01N 35/1002
   700/236
2017/0315144 A1  11/2017 Curel et al.

\* cited by examiner

FIG 7
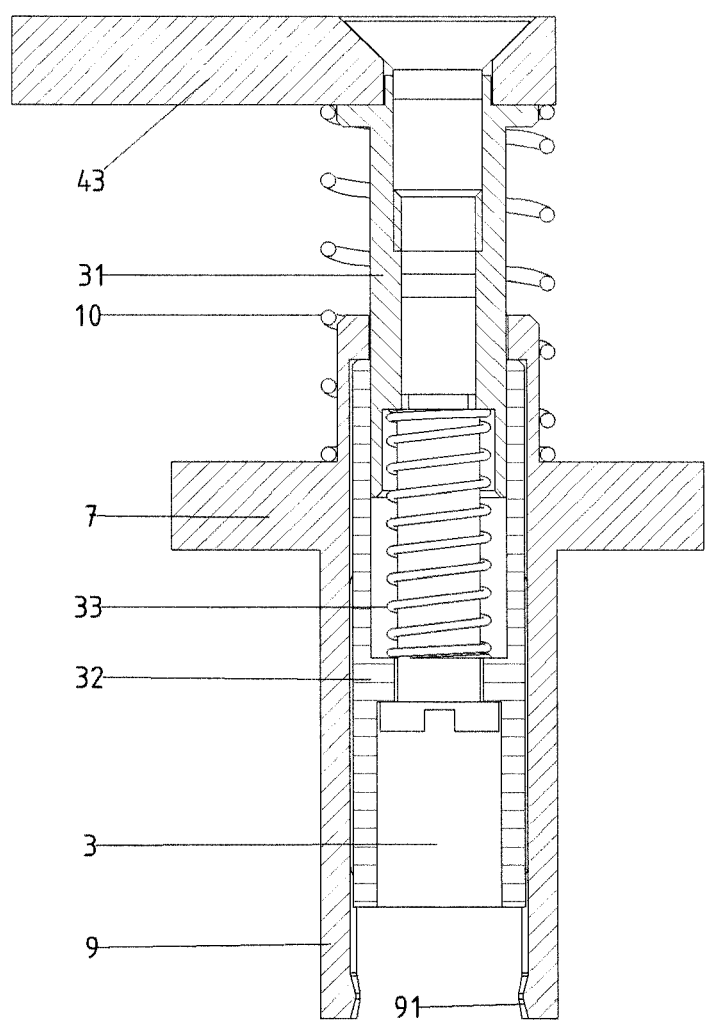
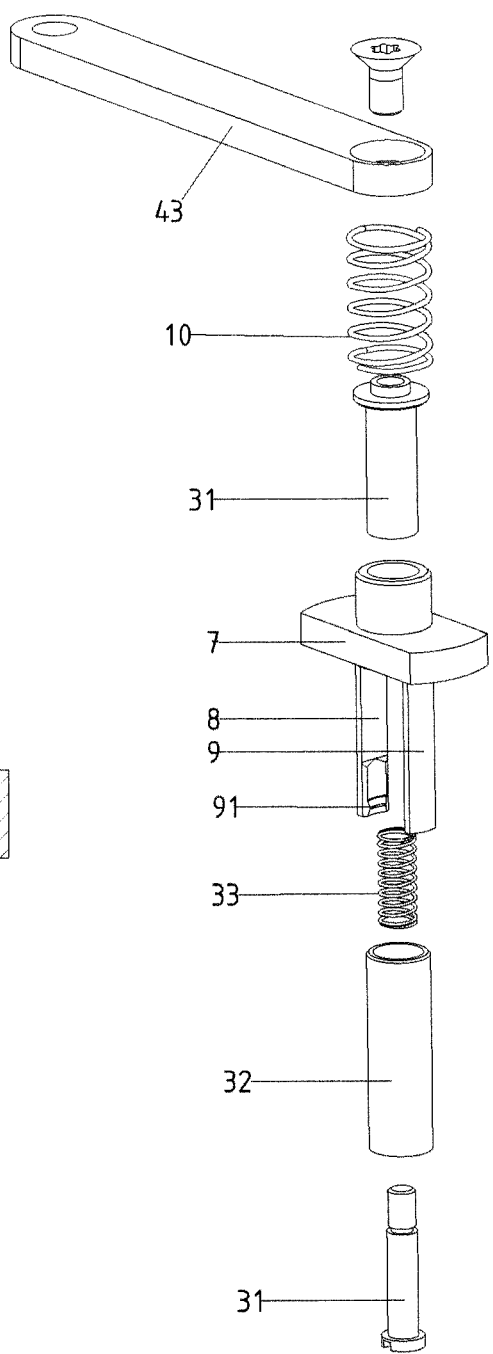

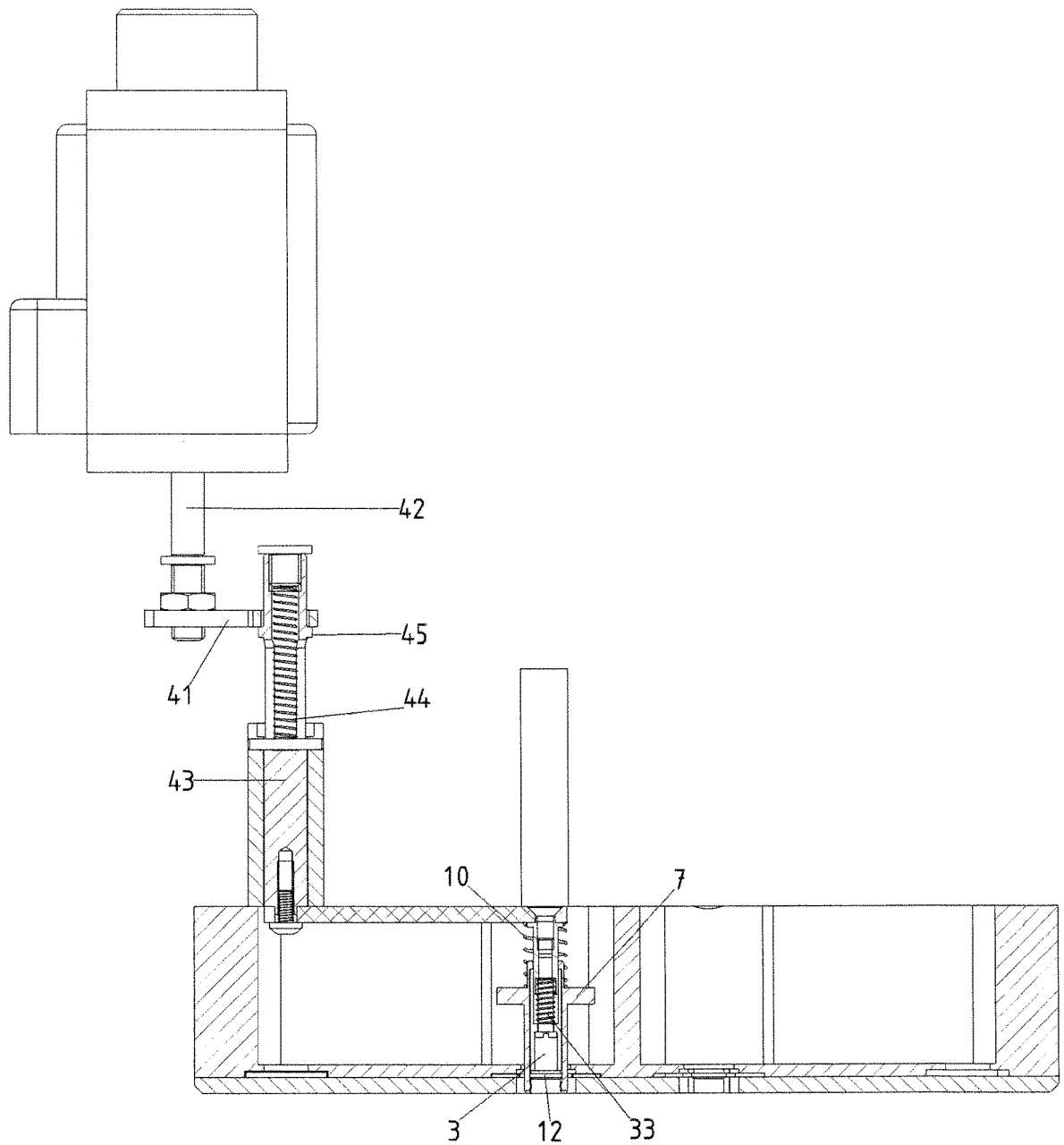

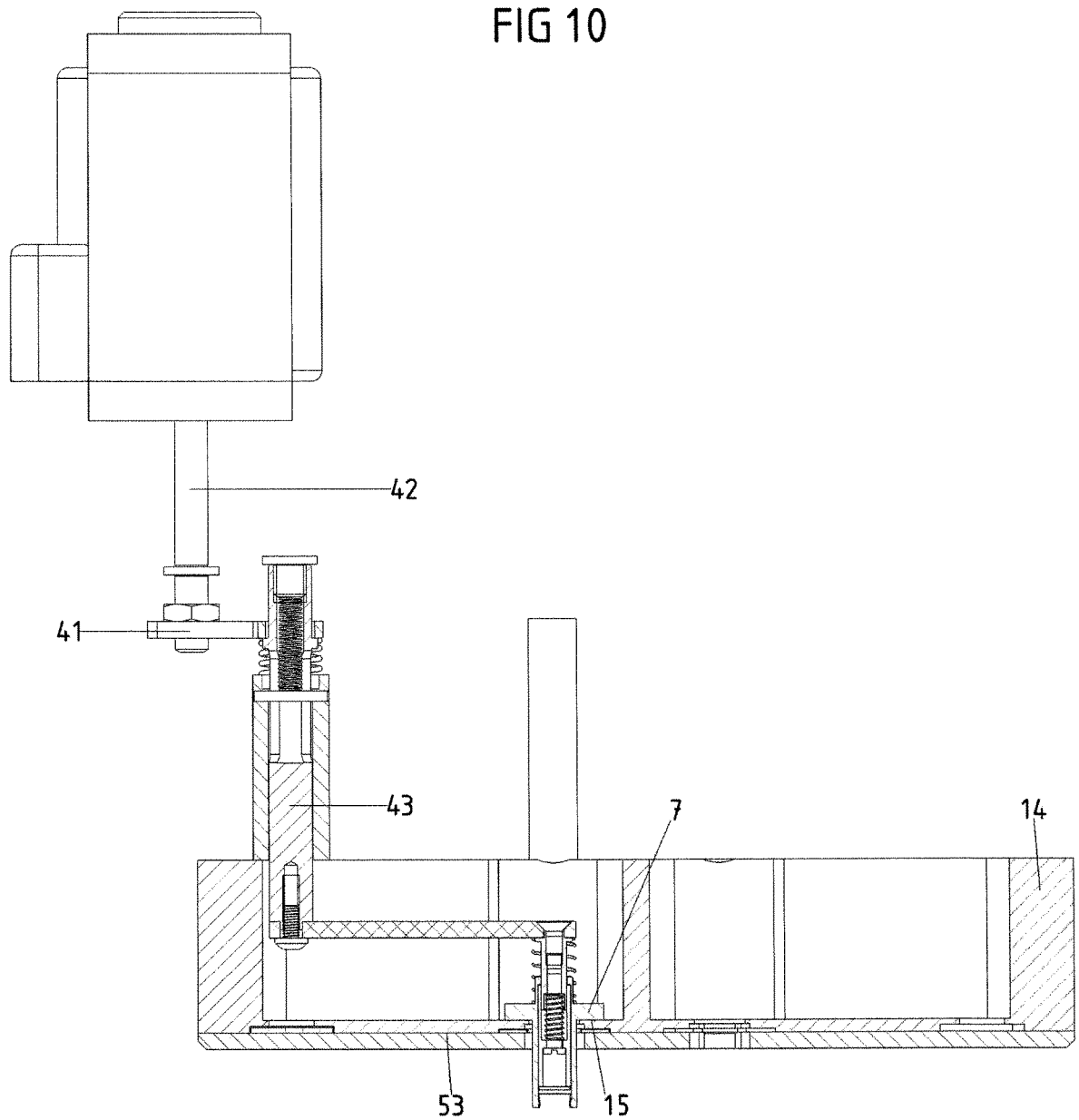

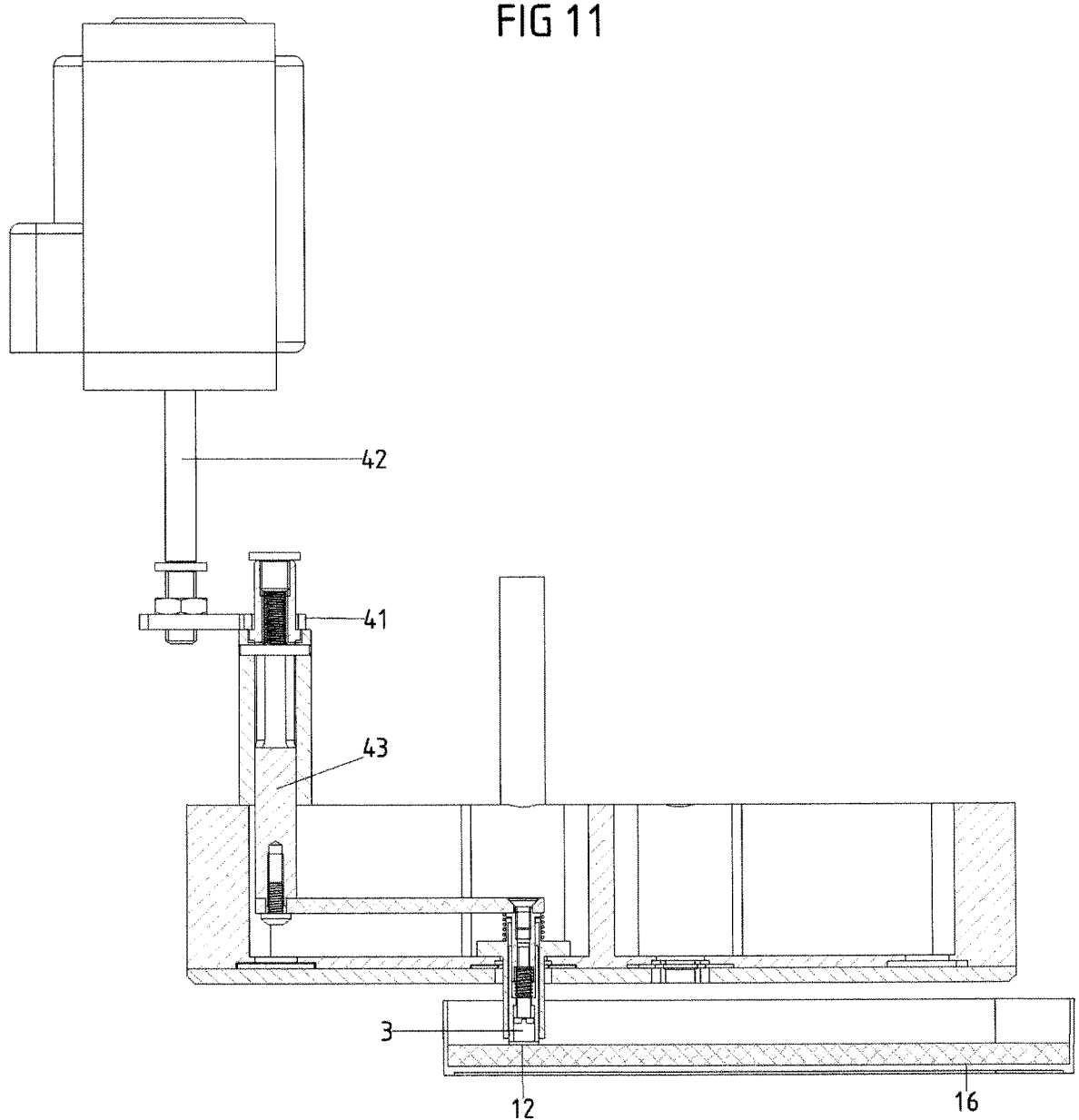

METHOD AND DEVICE FOR PLACING DISKS, SUCH AS ANTIBIOTIC DISKS

RELATED APPLICATION

This application is a National Phase of PCT/FR2017/052987 filed on Oct. 30, 2017, which claims the benefit of priority from French Patent Application Nos. 16 60775, filed on Nov. 8, 2016, the entirety of which are incorporated by reference.

The invention relates to a method and to a device for positioning disks, such as reactive disks, stored in the stacked state inside a cartridge, particularly on a culture support such as a Petri dish.

More specifically, it relates to a device for positioning disks comprising a zone for receiving a cartridge of disks, inside which zone at least one cartridge of disks can be stored, a piston laterally offset from the cartridge reception zone, means for moving the piston between a high position and a low position in order to allow, in the state in which the disk is positioned on the path followed by the piston, during the transition from the high position to the low position, the disk to be positioned on any surface positioned in line with the disk by pushing the piston on the disk, a transfer system capable of transferring a disk of the cartridge from the cartridge reception zone to a location, disposed on the path that can be followed by said piston during its transition from the high position to the low position, and which is called transit zone.

DESCRIPTION OF THE PRIOR ART

Cartridges pre-filled with reactive disks, i.e. with disks impregnated with an active substance, such as an antibiotic or an anti-fungal agent, and used with a view, for example, to test the sensitivity of microorganisms to said active substance, are well known to those versed in this art. The aim of these sensitivity tests is to identify the one or more active substance(s) able to kill or to inhibit the growth of microorganisms in a sample to be tested. In practice, the sample to be tested is placed on a culture medium, such as an agar of a Petri dish, and the disks are disposed on said agar. After incubation, the sensitivity can be determined visually, according to the appearance around the deposited disk.

Depositing these disks on the culture medium can be implemented using a manual activation device, as disclosed in U.S. Pat. No. 3,300,087, using a pneumatic actuator, as disclosed in document GB 2001432, or using a pricking needle, as disclosed in document EP 2518136. However, none of these devices is entirely satisfactory.

In the case of the device of the aforementioned American document, the disk, once it is ejected from the cartridge, drops under the effect of gravity so that, when the surface for receiving the disk is too far from the disk drop start point, there is a risk of incorrect positioning of the disk on the culture medium that can result in a non-compliant analysis result.

The device disclosed in the aforementioned British document requires the presence of a compressed air source, which is not always available in the places where such a positioning device can be installed.

The device disclosed in the aforementioned European document relates to a device that requires the disk to be pricked in order to be positioned. The detachment of the disk from the needle is not explained in this document. Therefore, there is again a risk of incorrect positioning.

International application WO 2016/071604 discloses a device for storing and selecting cartridges pre-filled with reactive disks to be positioned on a support, such as a Petri dish. Such a device comprises a pusher for transitioning the cartridge storage magazine from a position remote from a positioning opening to a position close to the positioning opening. The operations following this movement of the magazine, namely the ejection of a disk from the cartridge using transfer means and the positioning of the disk using a pusher, are not disclosed in detail. Consequently, this document does not disclose any solution for optimizing the positioning of a disk on a support.

AIMS AND SUMMARY

One aim of the invention is to propose a positioning device that is designed to enable assured positioning of the disk, including when the disk, positioned in line with the surface on which it must be positioned, is initially remote from said surface, by a significant distance that requires significant vertical travel of the disk.

Another aim of the invention is to propose a disk positioning device that ensures that the disk is positioned flat and in the desired location.

To this end, the aim of the invention is a device for positioning disks, such as reactive disks, stored in the stacked state inside a cartridge, said device comprising a zone for receiving a cartridge of disks, inside which zone at least one cartridge of disks can be stored, a piston laterally offset from the zone for receiving a cartridge of disks, means for moving the piston between a high position and a low position in order to allow, in the state in which a disk is positioned on the path followed by the piston, during the transition from the high position to the low position of the piston, the disk to be positioned on any surface positioned in line with the disk, by pushing the piston on the disk, a transfer system capable of transferring a disk of the cartridge from the cartridge reception zone to a location, disposed on the path that can be followed by said piston during its transition from the high position to the low position, and which is called transit zone, characterized in that the device comprises a disk movement assist guide that can be positioned in the transit zone and can move in a direction parallel to the up and down direction of movement of the piston.

By virtue of the presence of a disk movement assist guide at least partially disposed on the path followed by the piston during its transition from the high position to the low position, a disk is, in the state positioned on the path followed by the piston, assisted, even moved in a guided manner, on at least part of its vertical travel, by said movable guide that controls the movement of the disk. This results in the possibility of moving the disk away from the surface on which the disk has to be deposited by a greater distance than in the prior art. It is thus possible to deposit disks on culture supports placed on a movable support, along at least two axes, to allow quick and effective positioning of the disks with a reduced risk of error.

According to one embodiment of the invention, the disk movement assist guide is, during the transition of the piston from the high position to the low position, on part of the piston stroke, called first part of the piston stroke, axially movable, with the piston, in a direction parallel to the up and down direction of movement of the piston.

Thus, on this first part of the piston stroke, parallel to the movement of the piston, the disk movement assist guide guides the movement of the disk.

According to one embodiment of the invention, the disk movement assist guide is, during the transition of the piston from the high position to the low position, on a second part of the piston stroke following the first part of the piston stroke, in abutment against a stop of the device.

Thus, on this second part of the piston stroke, the disk movement assist guide is in abutment against a surface of the device forming a stop for keeping said guide in the fixed state. The piston thus can take over the guide to directly drive the disk by pushing on said disk.

According to one embodiment of the invention, the disk movement assist guide defines an axial through passage for receiving a disk, inside which passage the piston is, during its transition from the high position to the low position, able to slide to an end of travel position, in which it at least partially projects from the axial through passage.

The disk movement assist guide therefore defines a through passage for receiving a disk, with an axis parallel to the longitudinal axis of the piston, able to be covered by said piston, during the transition of the piston from the high position to the low position, said piston then, in the low position, at least partially projecting from said passage.

According to one embodiment of the invention, the disk movement assist guide assumes the form of a tubular body, preferably cylindrical, longitudinally split on at least part of its length in order to define two elastically deformable tabs, preferably with a curved internal profile, facing one another, said tabs being able to move apart from each other during the insertion of a disk that is able to be introduced between said tabs under the action of said transfer system.

According to one embodiment of the invention, the transfer system comprises a blade-holder support, with the blade of the blade-holder support extending parallel and above a substantially flat surface, called sliding surface, orthogonal to the longitudinal axis of the piston, and means for moving the blade-holder support on said sliding surface in a transverse direction, preferably orthogonal to the up and down direction of movement of the piston, in order to transition the blade of the blade-holder support from a position, in which it extends into the cartridge reception zone, to a position, in which it adjoins the disk movement assist guide, the blade of the blade-holder support being, in the state in which it is disposed in the cartridge reception zone, able to be positioned in abutment against the edge of a disk to be radially extracted from a cartridge in order to allow, through movement of the blade-holder support, the disk to be moved by being pushed from the cartridge toward the axial passage of the disk movement assist guide.

The transfer system thus ensures radial ejection of a disk from the cartridge and radial introduction of the disk into the axial through passage of the disk movement assist guide.

According to one embodiment of the invention, the means for moving the blade-holder support are at least partially common to the means for raising and lowering the piston, resulting in simplification of the device.

According to one embodiment of the invention, the blade is mounted with an at least axial clearance on said blade-holder support. This clearance prevents damage to the blade in the event that a disk is jammed inside a cartridge preventing its ejection.

According to one embodiment of the invention, the piston comprises a body and a piston head that is axially movable relative to the body between a position close to the body, i.e. a shorter length of the piston, and a position remote from the body, i.e. a longer length of the piston, said piston head being equipped with means for returning to the position remote from the piston body.

The assembly with axial clearance of the piston head allows, for example, absorption of a variation in thickness of the layer of the culture medium deposited in a culture support.

According to one embodiment of the invention, the means for returning the piston head to the position remote from the piston body are configured to exert a return force greater than 1.5 N, and preferably between 1.5 and 2 N.

According to one embodiment of the invention, the disk movement assist guide is equipped with means for returning to the position remote from the piston body. These return means allow independent movement of the disk movement assist guide and of the piston.

According to one embodiment of the invention, the disk movement assist guide is, in the high position of the piston, held by said return means in abutment against the piston head. This results in a better guarantee of simultaneous movement of the disk movement assist guide and of the piston head on part of the piston stroke.

A further aim of the invention is a method for positioning disks, such as reactive disks, stored in the stacked state inside a cartridge, using a positioning device of the aforementioned type, characterized in that the method comprises a step of positioning a disk of the cartridge in the transit zone, a step of assisting the movement of the disk, using the disk movement assist guide, in a direction parallel to the up and down direction of movement of the piston to an end of travel stop position of the disk movement assist guide, and a step of moving the disk using the piston under the action of a thrust exerted by the piston on the disk.

DESCRIPTION OF THE DRAWINGS

The invention will be better understood upon reading the following description of embodiments, with reference to the accompanying drawings, in which:

FIG. 7 shows, side-by-side, a schematic section view and an exploded position view of the elements of the piston/disk movement assist guide assembly according to the invention;

FIG. 9 shows a partial schematic section view of a device according to the invention, in the high position of the piston, in the state with a pellet inserted in the disk movement assist guide;

FIG. 10 shows a partial schematic section view of a device according to the invention, at the end of the first part of the piston stroke, in the position in abutment against the disk movement assist guide;

FIG. 11 shows a partial schematic section view of a device according to the invention, at the end of the second part of the piston stroke.

DETAILED DESCRIPTION

Figure 1:
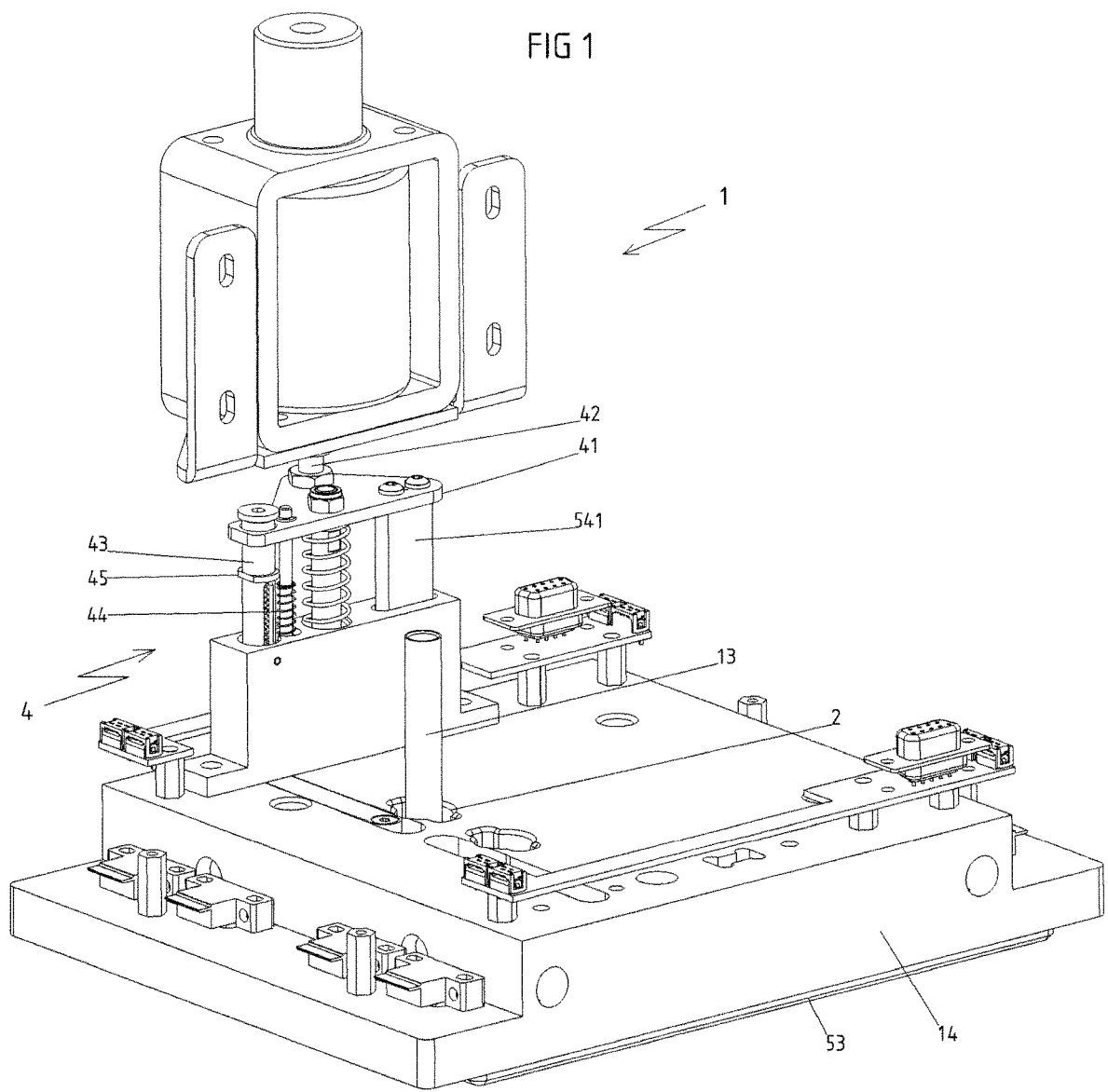
FIG. 1 shows a simplified partial perspective schematic view of a device according to the invention.
Figure 2:
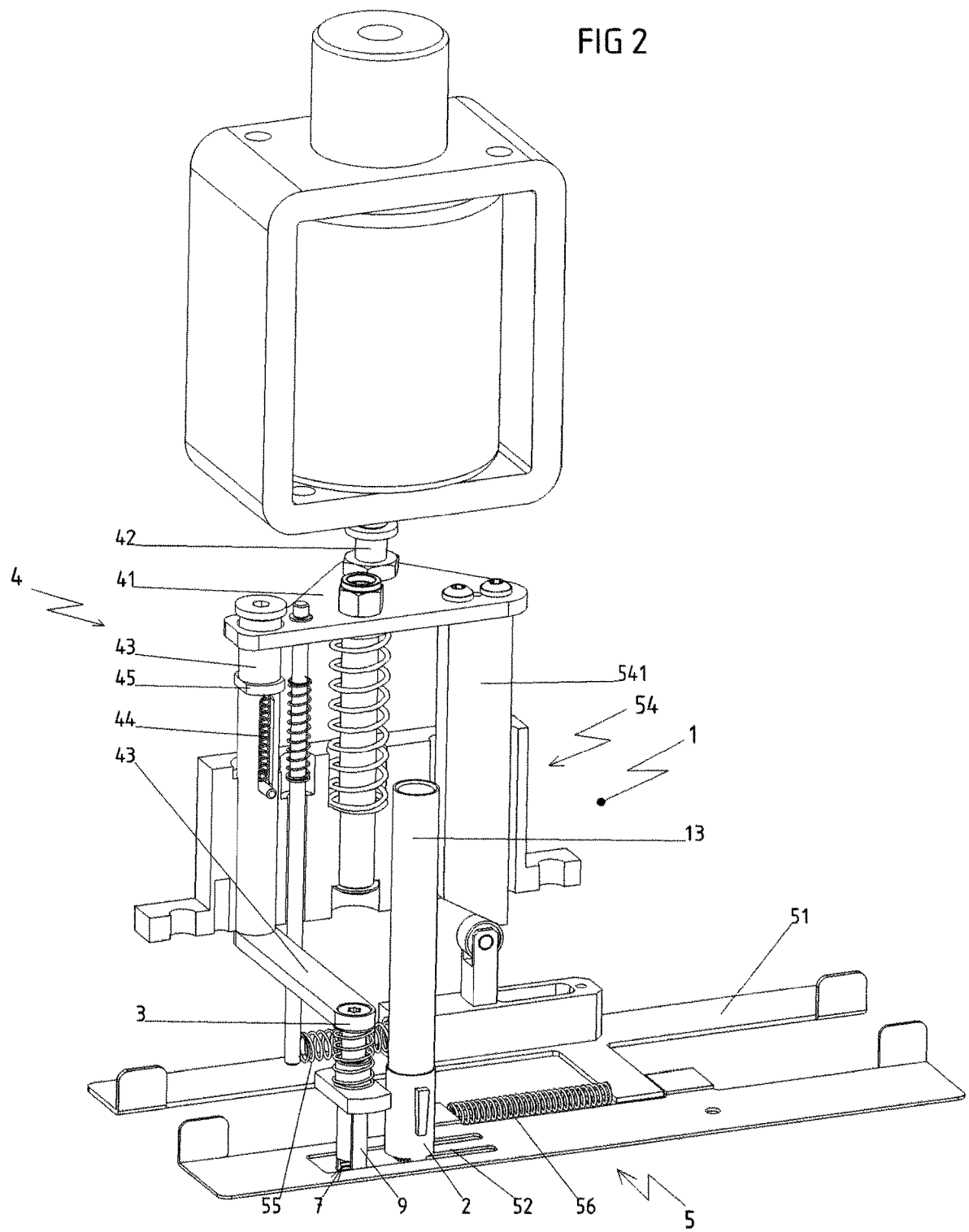
FIG. 2 shows a simplified partial perspective schematic view of a device according to the invention, in the high position of the piston, with the blade of the blade-holder support being disposed in the cartridge reception zone.
Figure 3:
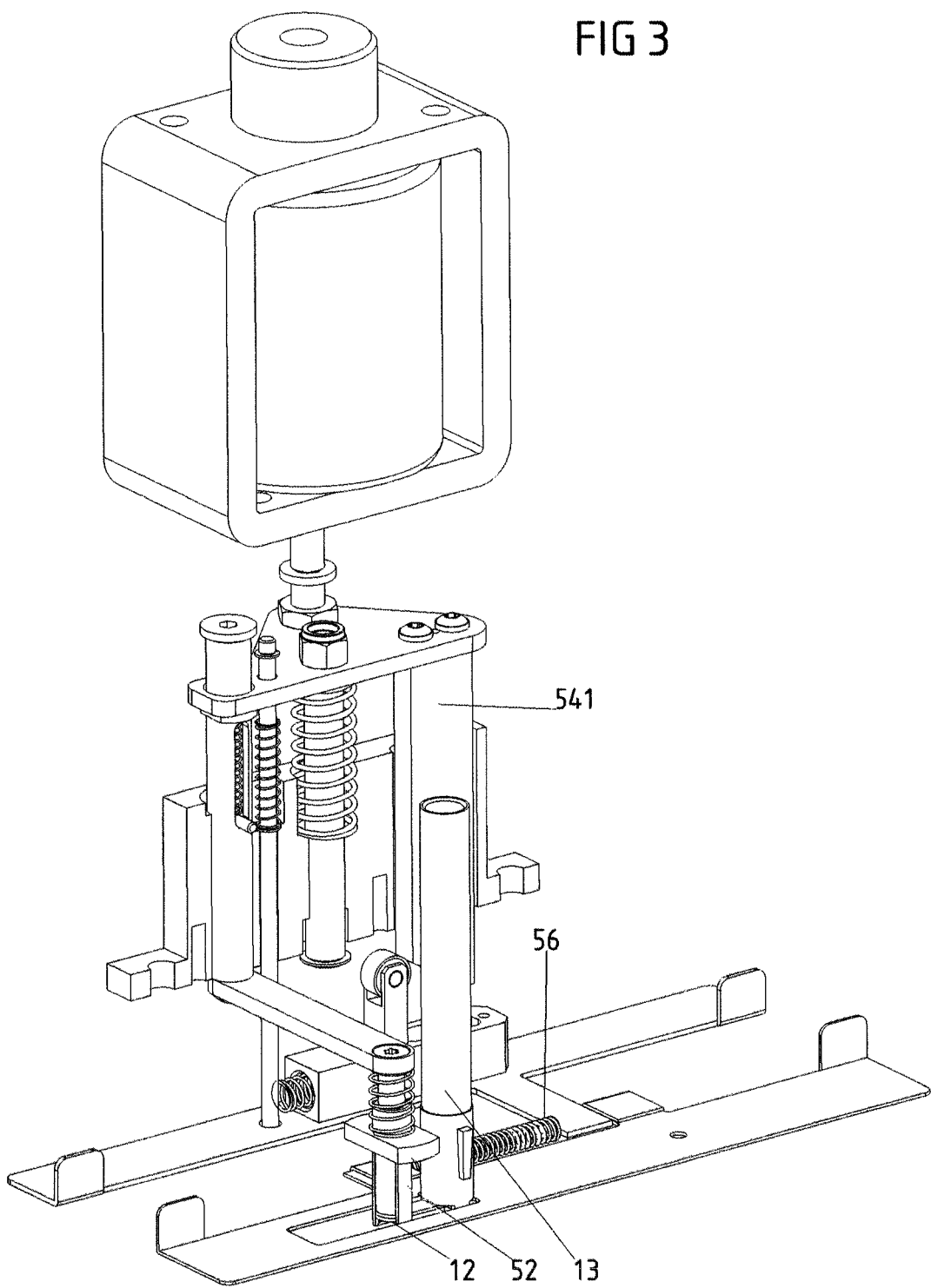
FIG. 3 shows a simplified partial perspective schematic view of a device according to the invention, in the high position of the piston, with the blade of the blade-holder adjoining the axial through passage of the disk movement assist guide.
Figure 4:
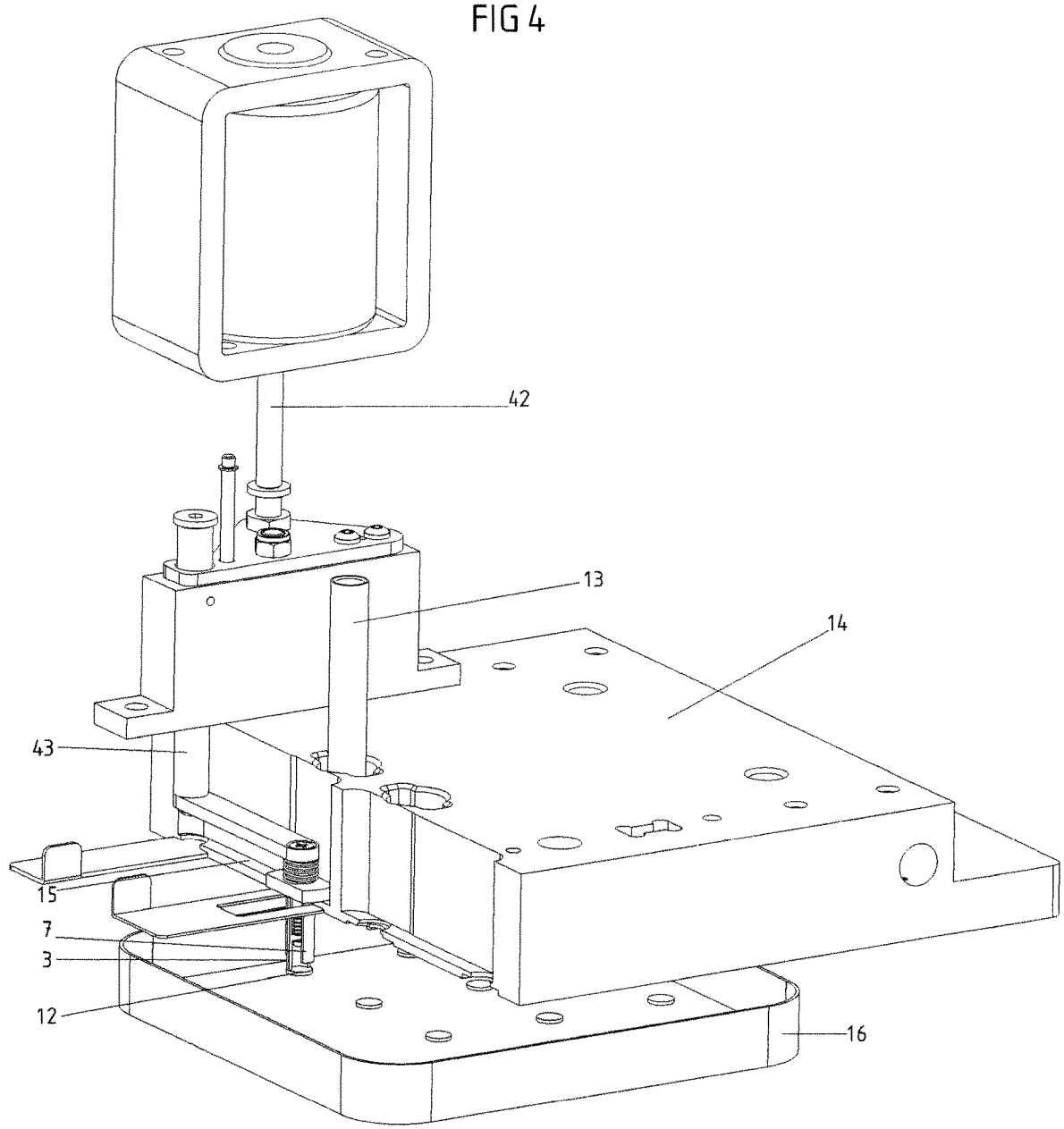
FIG. 4 shows a simplified partial perspective schematic view of a device according to the invention, at the end of the first part of the piston stroke, in the position in abutment against the disk movement assist guide.
Figure 5:
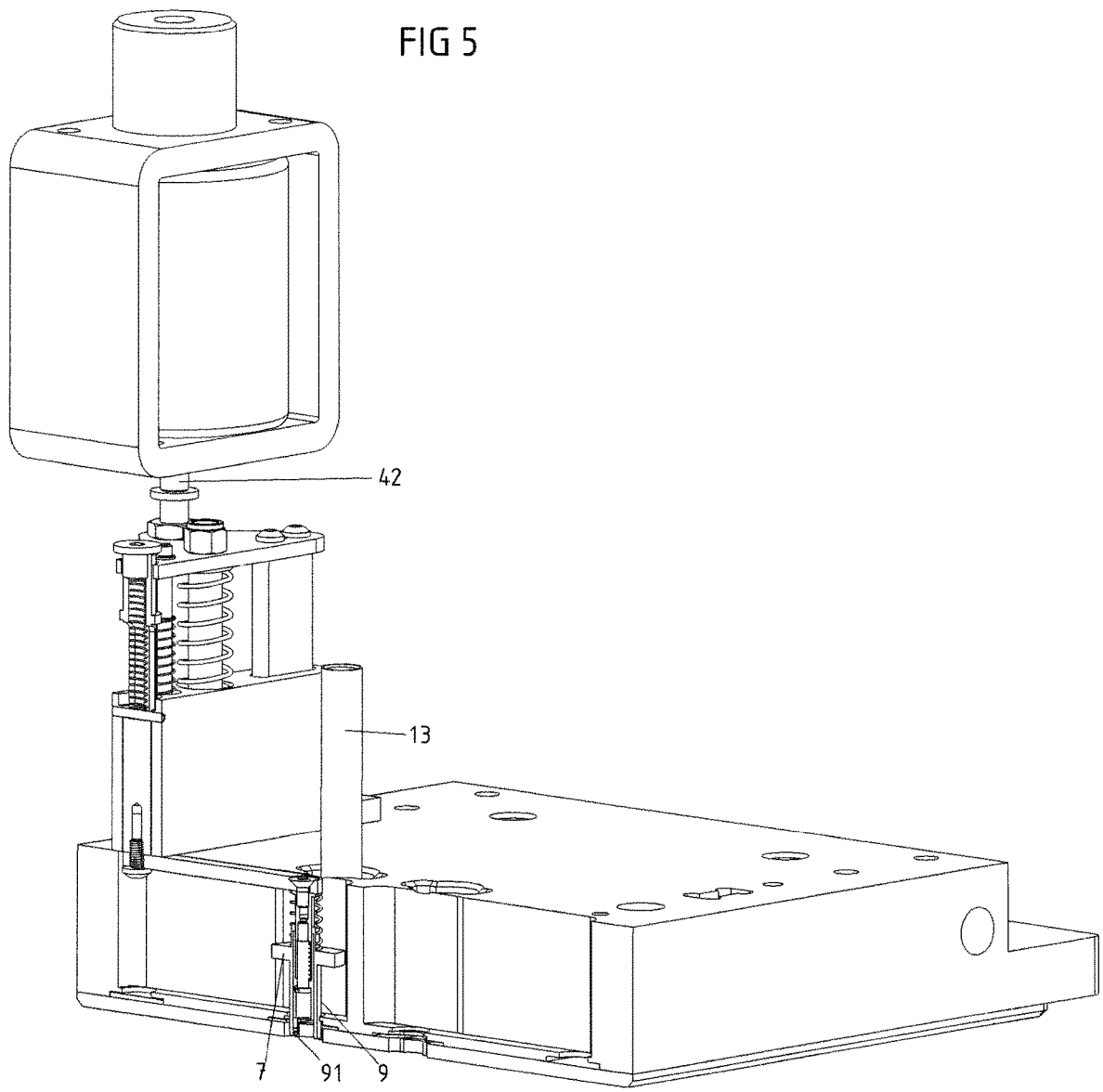
FIG. 5 shows a simplified partial schematic view, partially as a section view, of a device according to the invention, in the high position of the piston, the hidden blade of the blade-holder support being disposed in the cartridge reception zone.
Figure 6:
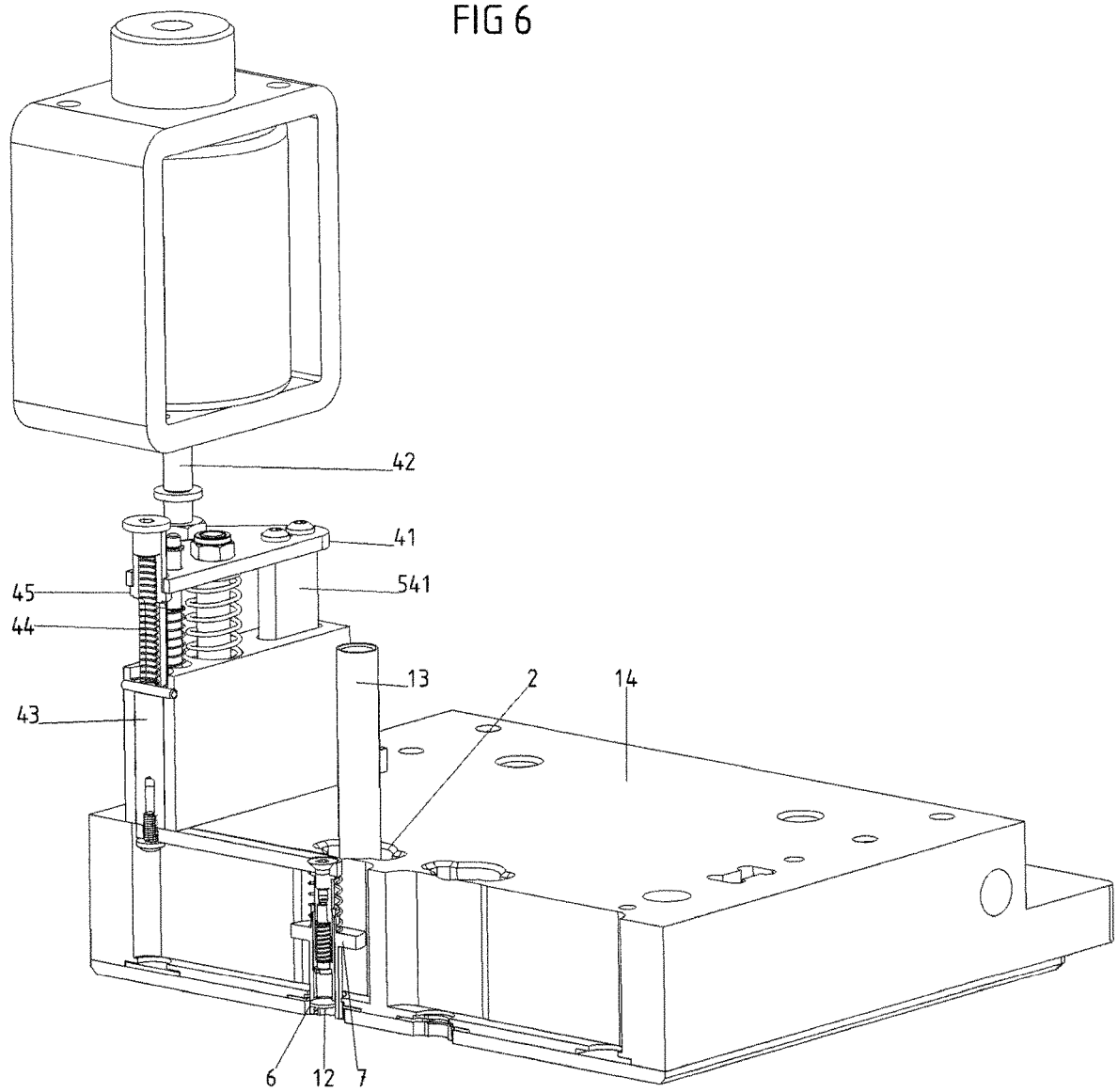
FIG. 6 shows a simplified partial schematic view, partially as a section view, of a device according to the invention, in the high position of the piston, the hidden blade of the blade-holder support being disposed adjoining the axial through passage of the disk movement assist guide, the disk being inside the disk movement assist guide.
Figure 8:
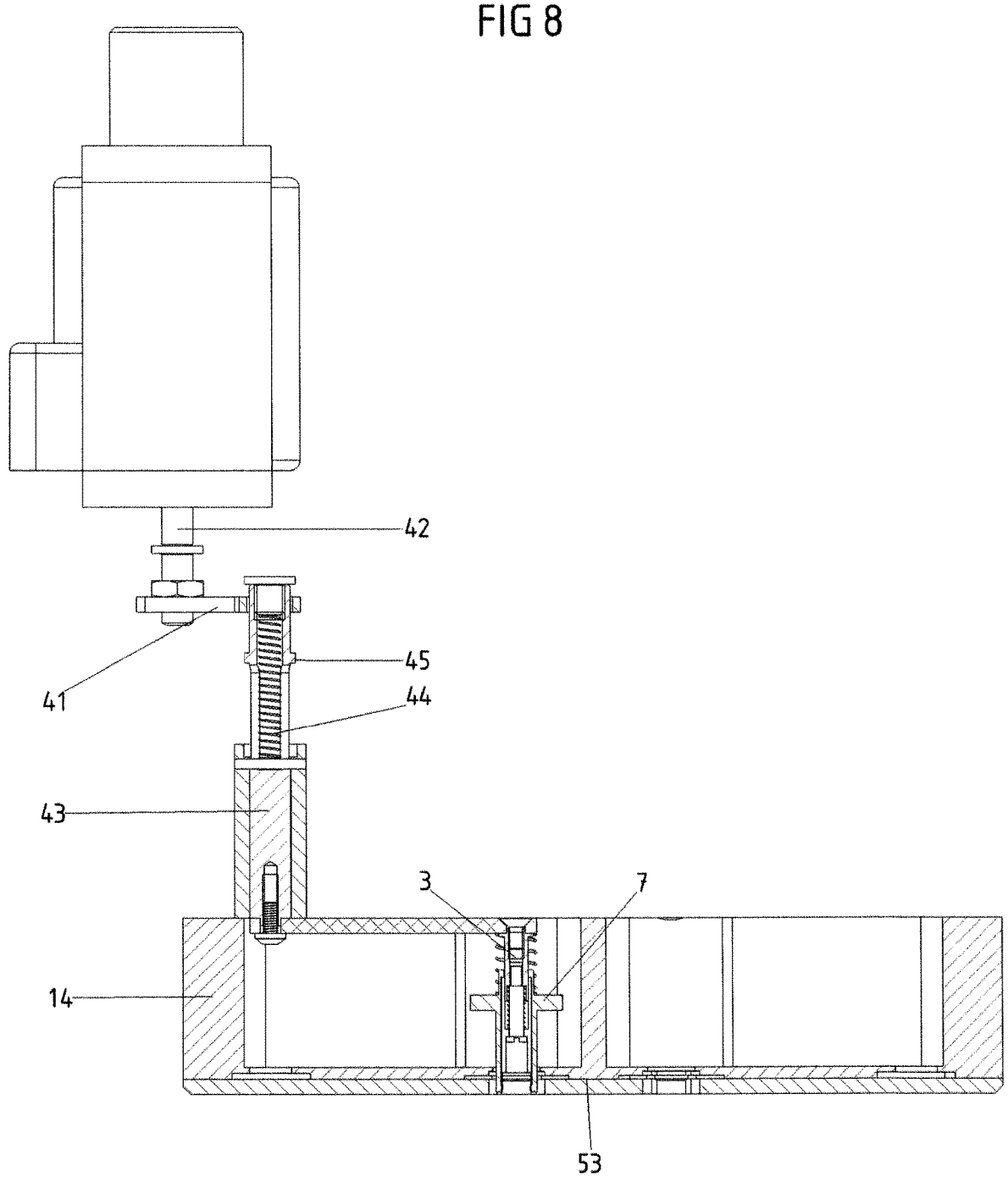
FIG. 8 shows a partial schematic section view of a device according to the invention, in the high position of the piston.

As stated above, the aim of the invention is a device and a method for positioning reactive disks 12 stored inside a cartridge 13 on a surface, such as a culture medium of a culture support, for example, a Petri dish 16. The cartridges 13 able to be used are well known to those versed in this art.

Each cartridge is in the form of a blind elongate tubular body, inside which the disks are stacked from the closed end to the open end, called disk distribution end, of said body, with a pusher being inserted between the disk closest to the closed end and said closed end, which pusher is spring loaded to return the stack of disks to the open end of the cartridge. This open end of the cartridge is provided with clips or tabs for retaining the disks inside the cartridge, against the action of the pusher. These tabs or clips define, in the vicinity of said open end, radial openings, through which the disks can be expelled from the cartridge one-by-one using a transfer system 5, which will be described hereafter.

Generally, the disks of the same cartridge are identical from one disk to the next, i.e. they support the same active substance. It is to be noted that the term "disk" must be understood in its broadest sense, and must be equated with "pellet" and particularly can apply to a shape that is not perfectly circular or does not have a constant thickness.

The device 1, which is the subject matter of the invention, therefore comprises a zone 2 for receiving a cartridge 13, inside which zone at least one cartridge of disks can be stored, generally in an upright position, with the open end of the cartridge turned toward the ground, in the operating configuration of the device.

In order to provide this cartridge reception zone 2, the device 1 comprises a support frame 14, in this case in the form of a hollow body defining a chamber, the top face of the chamber being provided with orifices, one of which forms the housing for receiving a cartridge kept in the upright state inside the chamber.

The positioning device 1 also comprises a piston 3, shown herein with a longitudinal axis parallel to the longitudinal axis of the cartridge 13, in the state in which the cartridge is inserted in the reception zone 2, and means 4 for moving the piston 3 between a high position and a low position in the operating configuration to allow, in the state in which a disk 12 is positioned on the path followed by the piston 3, during the transition from the high position to the low position, the disk 12 to be positioned on any surface, in this case the surface of a culture medium positioned in line with the disk 12, by pushing the piston 3 on the disk 12. In the example shown, the piston 3, and at least part of the means 4 for moving the piston, are at least partially inserted in the chamber defined by the support frame 14 in a location of the chamber adjoining the cartridge reception zone 2. The piston 3 is therefore laterally offset, i.e. in a direction transverse to the longitudinal axis of the piston, from the cartridge reception zone. Thus, the longitudinal axis of the cartridge and the longitudinal axis of the piston are not coincident and extend parallel to each other in the state in which the cartridge 3 is positioned in the reception zone 2. These volumes inside the chamber are connected together to allow the disk to transition from one housing to another and therefore from a position inside the cartridge to a position outside the cartridge disposed on the path of the piston. Indeed, the positioning device 1 comprises a transfer system 5 able to transfer a disk 12 of the cartridge 13 from the cartridge reception zone 2 to a location disposed on the path able to be followed by said piston 3 during its transition from the high position to the low position, and which is called transit zone 6.

Finally, the positioning device 1 comprises a disk movement assist guide 7 at least partially disposed on the path followed by the piston 3 during the transition of the piston 3 from the high position to the low position. This disk movement assist guide 7 can be positioned in the transit zone 6 and can be moved, from the transit zone 6, in a direction parallel to the up and down direction of movement of the piston 3. This disk movement assist guide 7 therefore assists the disk to the state in which it is ejected from the cartridge, i.e. outside the cartridge reception zone.

In the example shown, the disk movement assist guide 7 assumes the form of a cylindrical body positioned coaxial to the piston 3. This guide 7 is therefore at least partially housed in the same housing of the support frame 14 as the piston 3. The cylindrical body of the disk movement assist guide 7 is longitudinally split on part of its length in order to define two facing elastically deformable tabs 9. These tabs 9 have a curved internal profile in order to optimally match the external circular profile of the disk 12. The lower, inside internal end of these tabs 9 is provided with a protuberance 91 able to form a stop for retaining the disk inside said body. These tabs 9 are able to move apart from each other during the insertion of a disk 12 that is able to be introduced between said tabs 9 under the action of the transfer system 5, which will be described hereafter.

The cylindrical hollow body of the disk movement assist guide 7 therefore defines an axial through passage 8 for receiving a disk, inside which passage the piston 3 is, during its transition from the high position to the low position, able to slide to an end of travel position, in which it at least partially projects from the lower end of the axial through passage 8. The piston 3 thus allows, by pushing on the disk housed in the disk movement assist guide 7, the disk to be ejected from the disk movement assist guide 7. In the end of travel position, the piston projects from the bottom face of the chamber defined by the support frame.

In the example shown, this piston 3 comprises a body 31 and a piston head 32 that is axially movable relative to the body between a position close to the body 31, i.e. a shorter length of the piston 3, and a position remote from the body 31, i.e. a longer length of the piston 3. The piston head 32 is in the form of a tubular body provided with an internal peripheral shoulder. The body 31 of the piston is formed by two elements assembled together by screwing to allow the piston head to be threaded onto said body and to slide onto said body with the internal shoulder of the head able to form, via one of its lower faces, a stop preventing the disconnection of the head from the piston body by the lower end of the piston, and via the other one of its faces a support surface of an end of a helical spring coming into abutment via its other end on a stepped surface of the piston body. This spring, interposed between the piston head and body, therefore forms means 33 for returning the piston head 32 to the position remote from the piston body 31. In this return position, the piston head projects beyond the lower end of the piston body, as shown in FIG. 7. The assembly with axial clearance of the piston head allows, for example, when the piston is used to apply a thrust on a disk, a sudden impact to be absorbed between the disk and an obstacle, which impact could result, for example, in a variation in the thickness of the layer of the culture medium deposited in a culture support. The spring forming these means 33 for returning the piston head 32 to the position remote from the piston body 31 is, preferably, configured to exert a return force at least equal to 1.5 N, and preferably between 1.5 and 2 N.

The disk movement assist guide 7 is also threaded onto the piston 3 and is limited in terms of axial movement along the piston by part of the piston body and part of the piston head forming stops. The disk movement assist guide 7 is, in the state in which it is threaded on the piston, equipped with means 10 for returning to the remote position from the piston body 31 and is, in the high position of the piston, retained by said return means 10 in abutment against the piston head 32. These return means 10 comprise a helical spring surrounding the piston body and extending between two stops, one of which is disposed on the piston body, preferably in the vicinity of the upper end of the piston, the other one of which is disposed on the disk movement assist guide 7, this second stop being formed by an external peripheral collar of the cylindrical body forming the disk movement assist guide 7. In order to come into abutment against the piston head, in the example shown, the disk movement assist guide 7 has, at its upper end, opposite the end provided with tabs 9 and protuberances 91 from said tabs, an internal peripheral shoulder forming a means for retaining the guide 7 on said piston, by pressing this shoulder on the piston head in order to prevent disconnection of the disk movement assist guide 7 from the piston 3.

In order to move the piston 3 between a high position and a low position, and as a result the disk movement assist guide 7 threaded onto the piston 3, means 4, i.e. a mechanism, are provided for moving the piston 3. These means 4 for raising and lowering the piston between a high position, i.e. remote from the surface on which the disk must be deposited, and a low position, i.e. close to the surface on which the disk must be deposited, comprise a component 41, called motor, in this case formed by a plate that extends above and parallel to the top face of the chamber defined by the support frame 14. This motor component 41 can be raised and lowered in a direction parallel to the longitudinal axis of the piston 3 under the action of a control component 42, in this case formed by an electromagnet positioned above the plate forming the motor component 41. The means 4 for moving the piston 3 further comprise a control rod 43 disposed on the path followed by the motor component 41 and moved by the motor component 41 in the downward direction on completion of a first downstroke of the motor component 41. The role of this first downstroke of the motor component 41, without movement of the control rod 43 of the piston 3, will be described hereafter. The control rod 43 in this case is a curved rod coupled, at its lower end, to the piston 3, so that a downward movement of the rod results in a downward movement of the piston. Return means 44 comprising a spring are provided to return the control rod 43 to the high position. In the example shown, the control rod 43 passes through the plate forming the motor component in order to project, at its upper end, from the top face of the plate forming the motor component 41. This control rod 43 has an external peripheral collar 45 disposed on the path of the motor component 41 to allow, by pressing the motor component 41 on this collar, the movement of the control rod 43. Thus, during the downward movement of the plate forming the motor component 41, the plate slides along the control rod 43 to an abutment position on the collar of the control rod 43 to cause, as the downward movement continues, a simultaneous downward movement of the control rod 43, and as a result of the piston 3. The return means 44 tend to return the control rod 43 to the high position. Additional return means comprising a spring disposed between the support frame 14 and the motor component 41 are also provided to return the motor component 41 to the high position.

Part of these means 4 for raising and lowering the piston 3 also help to transfer a disk from the cartridge reception zone 2 to the transit zone 6, inside which the disk movement assist guide 7 is located in the high position of the piston 3.

Indeed, the device comprises, as stated above, a transfer system 5 able to transfer a disk 12 of the cartridge 13 from the cartridge reception zone 2 to a location called transit zone 6, disposed on the path able to be followed by said piston 3 during its transition from the high position to the low position, this transit zone 6 being equipped with the disk movement assist guide 7 in the high position of the piston. The purpose of the transfer system 5 is to radially eject a disk from the cartridge through the radial orifices of the cartridge.

This transfer system 5 comprises a blade-holder support 51, with the blade 52 extending parallel to and above a substantially flat surface 53, called sliding surface, orthogonal to the longitudinal axis of the piston 3. The sliding surface in this case is formed by a closure plate that forms the bottom face of the chamber defined by the support frame. The blade-holder support 51 and the blade are, for their part, disposed in the chamber defined by the support frame. This transfer system 5 further comprises means 54, i.e. a mechanism, for moving the blade-holder support 51 on said sliding surface 53 in a transverse direction, in this case orthogonal to the up and down direction of movement of the piston, in order to transition the blade 52 of the blade-holder support 51 from a position, in which it extends into the cartridge reception zone 2, to a position, in which it adjoins the disk movement assist guide 7, the blade 52 of the blade-holder support 51 being, in the state in which it is disposed in the cartridge reception zone 2, able to be positioned in abutment against the edge of a disk 12 to be radially extracted from the lower end of the cartridge to allow, through movement of the blade-holder support, the disk to be pushed from the lower end of the cartridge toward the axial passage 8 of the disk movement assist guide 7.

In the example shown, the means 54 for moving the blade-holder support 51 are at least partially common to the means 4 for raising and lowering the piston 3. In particular, these means 54 for moving the blade-holder support 51 comprise a component 41, called motor, in this case formed by a plate that extends above and parallel to the top face of the chamber defined by the support frame 14. This motor component 41 can be raised and lowered in a direction parallel to the longitudinal axis of the piston 3 under the action of a control component 42, in this case formed by an electromagnet positioned above the plate forming the motor component 41. It is to be noted that this motor component 41 and the control component 42 are the same as those used for raising and lowering the piston 3. To allow the blade-holder support 51 to move, the plate forming the motor component 41 supports a cam 541 that is active on said blade-holder support 51 during the first part of the downstroke of the motor component 41. The cam/blade-holder support cooperation results in a movement of the blade-holder in a direction orthogonal to the up and down direction of movement of the piston and the transition of the blade 52 of the blade-holder support 51 from a position, in which it extends into the cartridge reception zone 2, to a position, in which it adjoins the disk movement assist guide 7. The disk disposed at the lower end of the cartridge is thus transferred by pressing the blade on the edge of the disk of the cartridge reception zone 2 inside the axial through passage 8 of the disk movement assist guide 7. During this transfer, the piston 3 is kept in the high position despite the movement of the motor component 41, as explained above.

As stated above, in the examples provided, the means 54 for moving the blade-holder support 51 comprise a cam 541 supported by the same plate as that forming the plate of the motor component of the means for moving the piston. The cam and the plate forming the motor component 41 are raised and lowered by means of the same electromagnet as that moving the plate forming the motor component 41 of the means for moving the piston.

The cam 541, disposed on the face of the plate 41 forming the motor component opposite that which is subject to the action of the electromagnet, has a beveled end coming into abutment against an idler bearing component mounted on the blade-holder support 51 to allow, at the same time as the cam/plate assembly of the motor component is moved between a high position and a low position using the control component 42, a lateral movement of the blade-holder support 51 resulting from the cooperation, by abutment, of the inclined side formed by the bevel of the cam and the idler bearing component.

A return component 55, such as a spring, returns the blade-holder support 51 to the position in which the blade of said blade-holder support extends into the zone 2 for receiving the cartridge 13. In the example shown, the blade 52 is mounted with an at least axial clearance on said blade-holder support 51. To this end, a spring 56 is interposed between the blade and the rest of the blade-holder support. This spring 56 allows the blade to absorb any impacts, or to avoid being damaged, when a disk remains jammed in the cartridge or when the cartridge is empty, in spite of the thrust force exerted by the blade on the edge of the disk or on the base element of the empty cartridge. A sensor for detecting the position of the blade allows, in the event of an empty cartridge or of a jammed disk, the return of the piston 43 to be controlled.

In order to complete the assembly, means can be provided under the support frame 14 for moving the culture supports, in this case Petri dishes. These movement means can comprise a device for moving, on a horizontal plane along two orthogonal axes, the Petri dishes under the piston. These movement means are controlled by synchronism with the means for moving the piston and the means for moving the blade-holder support.

By virtue of the design of the positioning device as described above, the disk is positioned as follows:

A culture support is manually or automatically disposed under the piston 3, in line with the piston disposed in the high position. The motor component 41 is driven downward by the electromagnet and causes, on a first part of its stroke, cooperation of the cam 541 and of the blade-holder support 51 in order to move the blade 52 from the position, in which it extends into the cartridge reception zone 2, to a position, in which it adjoins the disk movement assist guide 7 disposed in the transit zone 6, causing, during this movement, by pressing on the edge of the disk 12 located furthest below the cartridge, a radial ejection of the disk 12 from the cartridge, and its introduction into the axial passage 8 of the disk movement assist guide 7. It is to be noted that in order to facilitate this insertion, the longitudinal edges of the tabs 9 of the disk movement assist guide 7 are chamfered. On completion of this first downward stroke of the motor component 41, continuing the downward movement of the motor component 41 causes movement of the piston 3 in the lowering direction of movement of the piston. This movement stroke of the piston between a high position and a low position is divided into a first part of the stroke, during which the disk movement assist guide 7 can be axially moved, with the piston, from the transit zone 6, in a direction parallel to the up and down direction of movement of the piston, in the downward direction. On completion of this first part of the stroke, the disk movement assist guide 7 is in abutment against a stop 15 of the device in order to keep the disk movement assist guide 7 in the fixed state as the downward movement of the piston continues on a second part of the stroke. The stop 15 in this case is formed by the closure plate forming the bottom face of the chamber defined by the support frame. In this stop position, the disk movement assist guide 7, and optionally the piston 3, partially project from the bottom face of the chamber defined by the support frame, as shown in FIG. 10, through an opening of said face. The external peripheral collar of the disk movement assist guide 7 is in abutment on the inner face of the closure plate of the chamber. When the downward movement of the piston continues on the second part of the piston stroke, the disk movement assist guide remains in abutment against the stop 15 of the device, particularly under the action of the return means 10 disposed between the piston body and the disk movement assist guide 7, so that its movement is prevented. The continuation of the downward movement of the piston causes the disk disposed in the axial passage of the disk movement assist guide 7 to be ejected out of the guide 7 under the action of a thrust of the piston sliding inside the disk movement assist guide 7, with this guide being kept fixed. If necessary, particularly when the agar layer inside the Petri dish is thicker than the desired thickness, the spring 33 disposed between the piston body 31 and head 32 compresses once the piston head is in contact, via the disk, with the agar, in order to prevent any damage of the agar, whilst keeping the disk applied on the agar. Once the positioning of the disk is complete, the control component 42 is returned to the high position, the motor component 41 is returned to the high position, as is the piston control rod 43, which, during its return, moves the disk movement assist guide 7 and causes it to return to the transit zone. At the same time, the blade-holder support is returned to the cartridge reception zone 2, and a new disk positioning cycle can begin.

In general, the positioning method therefore comprises a step of positioning a disk 12 of the cartridge in the transit zone 6, a step of assisting the movement of the disk 12 using the disk movement assist guide 7, in a direction parallel to the up and down direction of movement of the piston 3, to an end of travel stop position of the disk movement assist guide 7, and a step of the piston 3 moving the disk 12 under the action of a thrust exerted by the piston 3 on the disk 12.

The invention claimed is:

1. A device for positioning disks, stored in the stacked state inside a cartridge, said device comprising:
    a zone for receiving a cartridge of disks, inside which zone at least one cartridge of disks can be stored, a piston laterally offset from the zone for receiving a cartridge, means for moving the piston between a high position and a low position in order to allow, in the state in which a disk is positioned on the path followed by the piston, during the transition from the high position to the low position of the piston, the disk to be positioned on any surface positioned in line with the disk by pushing the piston on the disk, a transfer system capable of transferring a disk of the cartridge from the cartridge reception zone to a location, which is disposed on the path that can be followed by said piston during its transition from the high position to the low position and which is called a transit zone, wherein the device comprises a disk movement assist guide that can be positioned in the transit zone and can move in a direction parallel to the up and down direction of movement of the piston, wherein the disk movement assist guide defines an axial through passage for receiving a disk, inside which passage the piston is, during its movement from the high position to the low position, able to slide to an end of travel position, in which it at least partially projects from the axial through passage.

2. The device for positioning disks as claimed in claim 1, wherein the disk movement assist guide is, during the transition of the piston from the high position to the low position, on part of the piston stroke, called a first part of the piston stroke, axially movable, with the piston, in a direction parallel to the up and down direction of movement of the piston.

3. The device for positioning disks as claimed in claim 2, wherein the disk movement assist guide is, during the transition of the piston from the high position to the low position, on a second part of the piston stroke following the first part of the piston stroke, in abutment against a stop of the device.

4. The device for positioning disks as claimed in claim 1, wherein the disk movement assist guide assumes the form of a tubular body, longitudinally split on at least part of its length in order to define two elastically deformable tabs, facing one another, said tabs being able to move apart from each other during the insertion of a disk that is able to be introduced between said tabs under the action of said transfer system.

5. The device for positioning disks as claimed in claim 1, wherein the transfer system comprises a blade-holder support, with the blade of said blade-holder support extending parallel and above a substantially flat surface, called a sliding surface, orthogonal to the longitudinal axis of the piston, and means for moving the blade-holder support on said sliding surface in a transverse direction, in order to transition the blade of the blade-holder support from a position, in which it extends into the zone for receiving a cartridge, to a position, in which it adjoins the disk movement assist guide, the blade of the blade-holder support being, in the state in which it is disposed in the cartridge reception zone, able to be positioned in abutment against the edge of a disk to be radially extracted from a cartridge in order to allow, through movement of the blade-holder support, the disk to be moved by being pushed from the cartridge toward the axial passage of the disk movement assist guide.

6. The device for positioning disks as claimed in claim 5, wherein the means for moving the blade-holder support are at least partially common to the means for raising and lowering the piston.

7. The device for positioning disks as claimed in claim 5, wherein the blade is mounted with an at least axial clearance on said blade-holder support.

8. The device for positioning disks as claimed in claim 1, wherein the piston comprises a body and a piston head that is axially movable relative to the body between a position close to the body, i.e. a shorter length of the piston, and a position remote from the body, i.e. a longer length of the piston, said piston head being equipped with a first means for returning to the position remote from the piston body.

9. The device for positioning disks as claimed in claim 1, wherein the disk movement assist guide is equipped with a second means for returning to the position remote from a body of the piston.

10. A method for positioning disks, stored in the stacked state inside a cartridge, using a device for positioning disks according to claim 1, wherein the method comprises a step of positioning a disk of the cartridge in the transit zone, a step of assisting the movement of the disk, using the disk movement assist guide, in a direction parallel to the up and down direction of movement of the piston to an end of travel stop position of the disk movement assist guide, and a step of moving the disk using the piston under the action of a thrust exerted by the piston on the disk.

* * * * *